(12) United States Patent
Nagai et al.

(10) Patent No.: US 6,285,738 B1
(45) Date of Patent: Sep. 4, 2001

(54) HIGH-DEFINITION STILL PICTURE REAL-TIME DISPLAY TYPE X-RAY DIAGNOSTIC APPARATUS

(75) Inventors: Seiichiro Nagai; Koichiro Nabuchi, both of Tochigi (JP)

(73) Assignee: Kabushiki Kaisha Toshiba, Kawasaki (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/037,872

(22) Filed: Mar. 10, 1998

(30) Foreign Application Priority Data

Mar. 18, 1997 (JP) .................................. 9-064571

(51) Int. Cl.[7] ...................................... H05G 1/64
(52) U.S. Cl. .............................. 378/98.8; 378/98.3
(58) Field of Search .................. 378/98.8, 116, 378/98.3

(56) References Cited

U.S. PATENT DOCUMENTS 4,939,761 * 7/1990 Gall et al. .......................... 378/98.3
5,878,107 * 3/1999 Ishikawa et al. .................. 378/98.8

FOREIGN PATENT DOCUMENTS 4-227175 8/1992 (JP) .
5-276443 10/1993 (JP) .

* cited by examiner

*Primary Examiner*—Craig E. Church
(74) *Attorney, Agent, or Firm*—Oblon, Spivak, McClelland, Maier & Neustadt, P.C.

(57) ABSTRACT

When "fluoroscopy" is specified, a little amount of X rays are irradiated successively, and an X-ray image is reflected from rotating mirrors to enter a fluoroscopic camera head provided with FTCCD. The FTCCD can obtain a fluoroscopic image as a moving picture because successive imaging is possible in a frame rate. Moreover, when "radiography" is specified, great amounts of X rays are irradiated at one shot, and an X-ray image is reflected from the rotating mirrors to enter a radiographic camera head provided with FFTCCD. The FFTCCD is provided with pixels with large pixel size whose number is increased, and thus a high-definition radiographic image as a still picture can be obtained without using an X-ray film.

15 Claims, 8 Drawing Sheets

HIGH-DEFINITION STILL PICTURE REAL-TIME DISPLAY TYPE X-RAY DIAGNOSTIC APPARATUS

BACKGROUND OF THE INVENTION

1. Field of the Invention

The present invention relates to an X-ray diagnostic apparatus, more specifically, relates to an X-ray diagnostic apparatus which is capable of observing high-definition still pictures (radiographic pictures) at real time and recording the radiographic picture data electronically.

2. Description of the Related Art

Conventionally, there have been known an X-ray diagnostic apparatus having a portable holding unit which is portable by means of casters provided to its main body, or a set-type holding unit which is used to be set on a ceiling.

Figure 1:
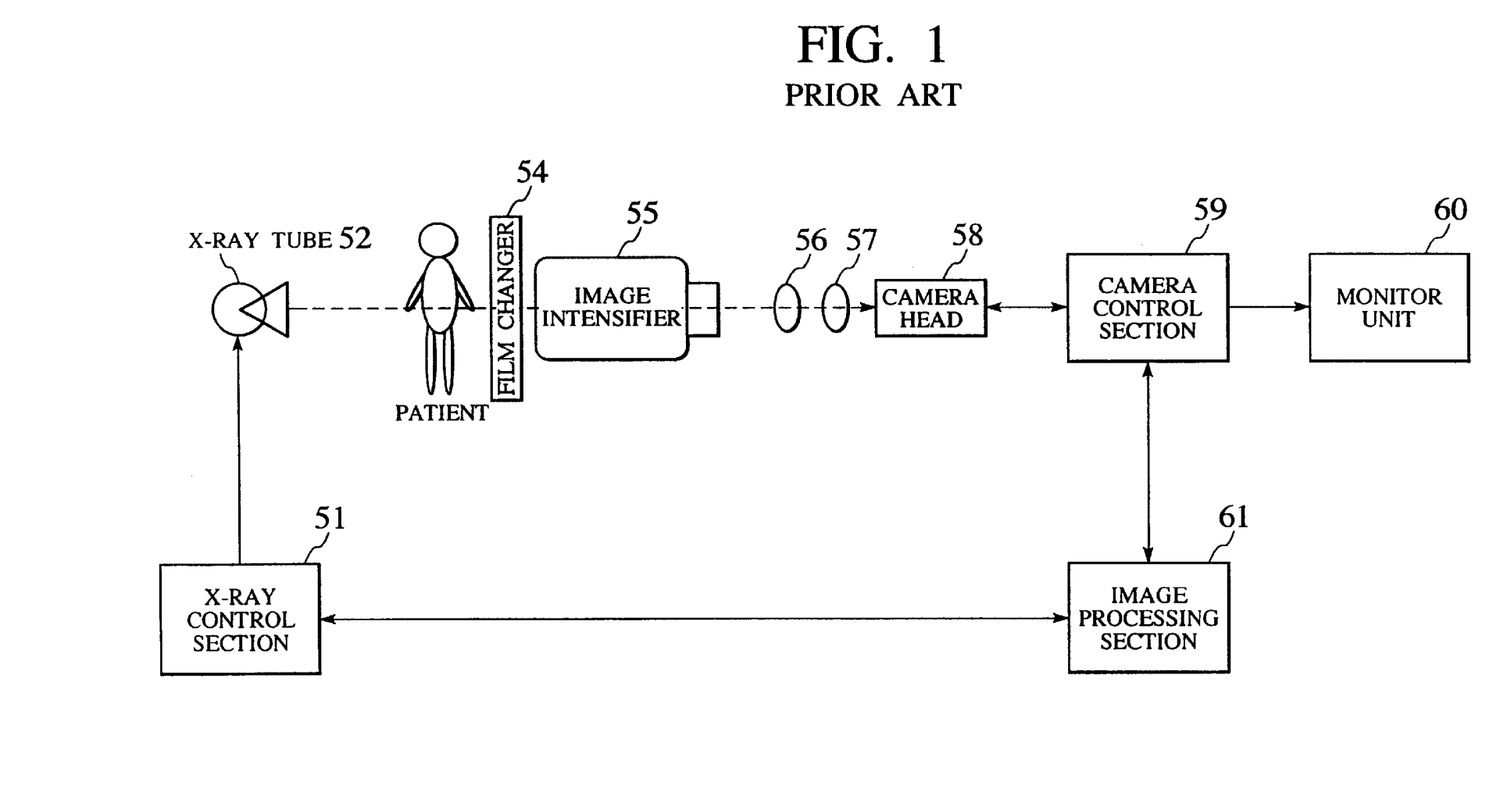
FIG. 1 is a block diagram of a conventional X-ray diagnostic apparatus.

This X-ray diagnostic apparatus, as shown in FIG. 1, has an X-ray control section 51 for controlling driving of an X-ray tube 52 which irradiates X rays to a patient, a film changer 54 for photographing an X-ray image in an X-ray film, an image intensifier 55 for converting the X-ray image into a visible light, and a camera head 58 for imaging the X-ray image based on the visible light from the image intensifier 55 through optical lenses 56 and 57.

In addition, this X-ray diagnostic apparatus has a camera control section 59 for controlling driving of the camera head 58, an image processing section 61 for performing a prescribed image process such as a video process on the X-ray image imaged by the camera head 58, a monitor unit 60 for displaying the X-ray image which was processed by the image processing section 61.

The X-ray tube 52 and image intensifier 55 are provided respectively to both end portions of a substantially C-shaped arm to face each other, for example, and when imaging, the X-ray tube 52 and image intensifier 55 are set so that a patient is located in the substantially middle portion therebetween (they sandwich the patient). When the X-ray tube 52 irradiates X rays to the patient, a formed X-ray image is captured by the image intensifier 55 to be converted into a visible light therein, and the visible light is imaged by the camera head so that the X-ray image is displayed on the monitor unit 60.

Here, in such an X-ray diagnostic apparatus, two kinds of imaging methods can be used. They are "fluoroscopy" in which a little amount of X rays are irradiated successively so that a moving picture is obtained, and "radiography" in which great amounts of X rays are irradiated at one shot so that a still picture is obtained. These "fluoroscopy" and "radiography" are selectively used according to cases.

In other words, in general, "fluoroscopy" is performed first. When the "fluoroscopy" is specified by an operator, the X-ray control section 51 shown in FIG. 1 controls driving of the X-ray tube 52 so that the X-ray tubes 52 irradiates a little amount of X rays successively. As a result, an X-ray image is formed through a patient. This X-ray image is converted into the X-ray image of a visible light by the image intensifier 55 to be imaged by the camera head 58. Then, the X-ray image is subject to the prescribed image process in the image processing section 61, and the X-ray image is supplied to the monitor unit 60 to be displayed thereon.

Since a little amount of X rays are irradiated in the "fluoroscopy" in order to reduce an amount of exposure, resolution of an obtained image (fluoroscopic image) and image quality such as S/N are not much satisfactorily, but since X rays are irradiated successively, a moving picture can be obtained. The operator chooses the proper time according to the moving picture and specifies "radiography" in desired timing.

When the "radiography" is specified by the operator, the X-ray control section 51 shown in FIG. 1 drives and controls the X-ray tube 52 so that the X-ray tube 52 irradiates great amounts of X rays at one shot. As a result, an X-ray image is formed through the patient. This X-ray image is printed in an X-ray film provided to the film changer 54.

Since this "radiography" is performed by the manner that X rays are irradiated at one shot, an obtained image (radiographic image) becomes a still picture, but great amounts of X rays are irradiated, so the radiographic image with excellent resolution and high quality such as S/N can be printed in the X-ray film. Then, a doctor makes diagnosis based on the radiographic image obtained by developing the X-ray film.

However, in the conventional X-ray diagnostic apparatus, there arose problems such that since radiographic image was obtained by printing it in the X-ray film, the radiographic image could not be checked until the X-ray film was developed, so in the cases where photography becomes failure and the picture of a desired affected part came out badly, it was necessary to radiograph again, and a wide space was required for X-ray films in which radiographic images were printed.

For this reason, it is desired to develop an X-ray diagnostic apparatus which can display also a radiographic image as well as a fluoroscopic image on the monitor unit, and can record the radiographic image in a data base electronically.

If such an X-ray diagnostic apparatus is developed, the following advantages can be obtained. A radiographic image can be checked on the monitor unit immediately without developing the radiographic image, and if the radiography becomes failure, the radiography can be performed again immediately. Further, since electronic storage becomes possible, reference becomes easy, and there is no difficulty in a storage place for the radiographic images.

However, since the conventional X-ray diagnostic apparatus was capable of imaging a moving picture by means of fluoroscopy, a so-called frame transfer, interline transfer or frame interline transfer CCD image sensor (FTCCD, ITCCD and FITCCD) which can be driven at high speed as the camera head 58 was provided. Therefore, when this CCD image sensor was used for the "radiography", resolution of an obtained radiographic image was deteriorated worse than that in an X-ray film, and thus a radiographic image which was useful for a diagnosis could not be obtained.

Namely, when such an CCD image sensor receives an X-ray image which was converted into a visible light by the image intensifier 55, all electric charges of the X-ray image are transferred into a light shielding area (memory area) at high speed in vertical interval time code, and they are read in order based on a driving clock (horizontal transfer). For this reason, the CCD image sensor is suitable for imaging a moving picture such as "fluoroscopy", but since a spatial sampling frequency is limited, it is limited to improve image quality, and thus the CCD image sensor could not be used for "radiography".

Accordingly, in the conventional X-ray diagnostic apparatus, at the time of "radiography", a high-definition radiographic image was obtained by printing the radiographic image in an X-ray film.

The number of pixels of the CCD image sensor should be increased in order to obtain a high-definition radiographic image in FTCCD, ITCCD and FITCCD, but if the number of pixels is increased without changing a size of the pixels (pixel size), there arises new problems that a whole CCD chip becomes large, and the number of chips obtained from one silicon wafer is reduced, so cost becomes high.

On the contrary, if a number of pixels is increased with the pixel size being small, the whole CCD chip becomes small, and thus the number of chips obtained from one silicon wafer is increased, but there arises new problem such that the number of saturation electrons which can be accumulated in one pixel is reduced, and excellent S/N characteristic cannot be obtained. This is because the S/N characteristic of the CCD image sensor is determined by quantum fluctuation of the number of electrons caused in pixels, and thus more satisfactory S/N characteristic can be obtained when the number of electrons is larger (pixel size is larger).

Accordingly, it is difficult to use FTCCD, ITCCD and FITCCD for the radiography with increasing the number of pixels.

Here, examples of the CCD image sensor existing except for FTCCD are full-frame CCD (FFTCCD), interline transfer CCD (ITCCD) and frame interline transfer CCD (FITCCD), but FFTCCD (full-frame CCD) is suitable for increasing the number of pixels from the viewpoints of the costs and S/N characteristic.

Namely, since FFTCCD has no light shielding area unlike another CCD image sensors and the pixels which are arranged in parallel in a vertical direction serve also as a vertical transfer path of electric charges, the pixel size is set to be larger, and further the whole chip size can be reduced, so FFTCCD is suitable from the viewpoints of the costs and S/N characteristic. For this reason, by means of FFTCCD, a high-definition radiographic image can be obtained.

However, since the FFTCCD has no light shielding area unlike FTCCD, an image signal cannot be outputted during accumulation of electric charges, and electric charges cannot be accumulated in each pixel during output of the image signal (a light cannot enter each pixel). For this reason, FFTCCD is necessary to be driven in at least intervals of an image output period, so if fluoroscopy is performed by using FFTCCD, successive irradiation of X rays is driven at interval of the image output period. As a result, a moving picture cannot be imaged satisfactorily. For this reason, when FFTCCD is provided in order to obtain a high-definition radiographic image, "fluoroscopy" is troubled.

SUMMARY OF THE INVENTION

The present invention is devised in order to solve the aforementioned problems, and it is an object of the present invention to provide an X-ray diagnostic apparatus which is capable of "radiography" using solid imaging means and of obtaining a satisfactory moving picture (fluoroscopic image) at the time of fluoroscopy, and high-definition still picture (radiography image) at the time of radiography.

In order to achieve the above object, the present invention provides an X-ray diagnostic apparatus including: X-ray generating means for irradiating an examinee with X rays; X-ray generation control means for controlling driving of the X-ray generating means so as to irradiate a little amount of X rays successively at the time of fluoroscopy and controlling driving of the X-ray generating means so as to irradiate great amounts of X rays at one shot at the time of radiography; X-ray/visible-light converting means for converting an X-ray image, which was formed by irradiating the examinee with X rays by the X-ray generating means at the time of fluoroscopy and radiography, into a visible light; optical path changing means for selectively changing an optical path for the X-ray image of visible light from the X-ray/visible-light converting means according to the fluoroscopy and radiography; first solid imaging means for receiving the X-ray image of visible light whose optical path was changed by the optical path changing means at the time of the fluoroscopy to form a fluoroscopic image; and second solid imaging means for receiving the X-ray image of visible light whose optical path was changed by the optical path changing means at the time of the radiography to form a radiographic image.

As the "X-ray/visible-light converting means", for example, an image intensifier can be used. Moreover, a fluorescent membrane may be provided in front of each pixel of the solid imaging means so that the X rays are converted into a visible light by the fluorescent membrane and the visible light enters each pixel.

In such an X-ray diagnostic apparatus, the first solid imaging means used for fluoroscopy and the second solid imaging means used for radiography are selected according to fluoroscopy and radiography to be used, namely, this apparatus has two-head structure, so a moving picture (fluoroscopic image) at the time of fluoroscopy and a high-definition still picture (radiographic image) at the time of radiography can be obtained by using the solid imaging means.

In suitable embodiment of the present invention, the second solid imaging means is a solid image sensor for directly and vertically transferring electric charges accumulated in an imaging section thereof to a horizontal transfer path, and is such a solid state sensor that the number of pixels thereof are more than the number of pixels of the first solid imaging means.

In suitable embodiment of the present invention, the X-ray diagnostic apparatus further includes X-ray shielding means for shielding the X rays irradiated from the X-ray generating means according to a portion of the examinee to be imaged to adjust an irradiated area.

In suitable embodiment of the present invention, the X-ray diagnostic apparatus wherein the second solid imaging means is provided so that a horizontal scanning direction thereof coincides with a direction of the examinee's height, further includes: storage means for temporarily storing the radiographic image from the second solid imaging means therein in the order of the horizontal scanning of the second solid imaging means; and reading control means for reading the radiographic image stored in the storage means along a direction which intersects perpendicularly to the horizontal scanning direction of the second solid imaging means.

In suitable embodiment of the present invention, the X-ray diagnostic apparatus further includes driving control means for when the irradiated area is adjusted by the X-ray shielding means, controlling reading of the second solid imaging means so as to read unnecessary electric charges to be a non-irradiated area with X rays at high speed to seep away the unnecessary electric charges to a drain area, and so as to read valid electric charges to be the irradiated area with X rays successively.

In suitable embodiment of the present invention, the driving control means controls reading of the second solid imaging means so as to end reading of electric charges in a frame when reading of valid electric charges is ended, and when electric charges in next frame are read, sweep away unnecessary electric charges in previous frame as well as unnecessary electric charges in the current frame to the drain area.

In suitable embodiment of the present invention, the X-ray diagnostic apparatus further includes driving control means for when the irradiated area is adjusted by the X-ray shielding means, controlling reading of the second solid imaging means so as to read unnecessary electric charges to be a non-irradiated area with X rays at high speed and add the unnecessary electric charges in a horizontal transfer path to output the unnecessary electric charges, and so as to read valid electric charges to be the irradiated area with X rays successively.

In addition, in order to achieve the above object, the present invention provides an X-ray diagnostic apparatus, including: X-ray generating means for irradiating an examinee with X rays; X-ray generation control means for controlling driving of the X-ray generating means so as to irradiate a little amount of X rays successively at the time of fluoroscopy and controlling driving of the X-ray generating means so as to irradiate great amounts of X rays at one shot at the time of radiography; X-ray/visible-light converting means for converting an X-ray image, which was formed by irradiating the examinee with X rays by the X-ray generating means at the time of fluoroscopy and radiography, into a visible light; X-ray shielding means for shielding the X rays irradiated from the X-ray generating means according to a portion of the examinee to be imaged to adjust an irradiated area; and solid imaging means in which electric charges accumulated in its imaging section are vertically transferred to a horizontal transfer path directly and which is provided so that a horizontal scanning direction thereof coincides with a direction of the examinee's height, the solid imaging means for receiving an X-ray image of visible light from the X-ray/visible-light converting means to form a fluoroscopic image.

The nature, principle and utility of the invention will become more apparent from the following detailed description when read in conjunction with the accompanying drawings.

DETAILED DESCRIPTION OF THE PREFERRED EMBODIMENTS

The following details preferable embodiments of a high-definition still picture real time display-type X-ray diagnostic apparatus of the present invention on reference with the drawings.

Figure 2:
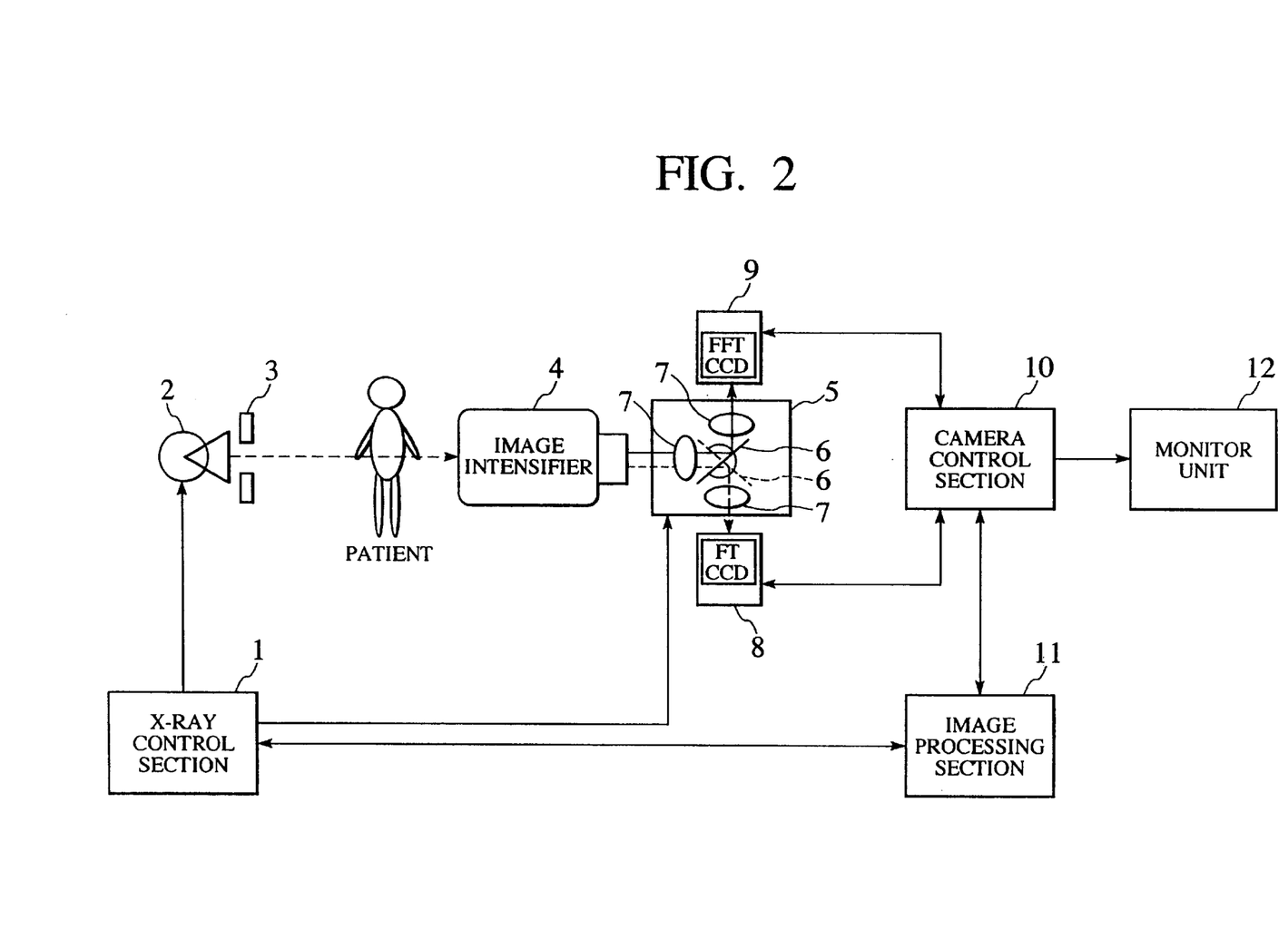
FIG. 2 is a block diagram of an X-ray diagnostic apparatus according to embodiment of the present invention.

The X-ray diagnostic apparatus according to embodiment of the present invention, as shown in FIG. 2, has an X-ray control section 1 for controlling an amount of X rays at the time of "fluoroscopy" and "radiography", an X-ray tube 2 for irradiating a little amount of X rays to an examinee (patient) successively at the time of "fluoroscopy" by control through the X-ray control section 1 and for irradiating great amounts of X rays to the examinee at one shot at the time of "radiography", and an X-ray shielding section 3 for shielding the X rays from the X-ray tube 2 so that only a desired affected part is irradiated with the X rays at the time of "radiography".

As for the "fluoroscopy" in which irradiation with a little amount of X rays may be performed successively, irradiation with X rays may be performed successively, or irradiation with X rays may be performed intermittently in each frame unit, for example (pulse fluoroscopy: this is also successive irradiation broadly).

In addition, this X-ray diagnostic apparatus has an image intensifier 4, an optical path changing section 5 composed of rotating mirrors 6 and optical lenses 7, a fluoroscopic camera head 8 and a radiographic camera head 9. The image intensifier 4 converts an X-ray image formed such that the examinee is irradiated with X rays into an X-ray image of a visible light. The optical path changing section 5 selectively changes an optical path of the X-ray image converted into the visible light by the image intensifier 4 according to the "fluoroscopy" and "radiography". The fluoroscopic camera head 8 receives the X-ray image whose optical path was changed by the optical path changing section 5 at the time of "fluoroscopy" and generates a fluoroscopic image signal. The radiographic camera head 9 receives the X-ray image whose optical path was changed by the optical path changing section 5 at the time of "radiography" and generates a radiographic image signal.

In addition, the X-ray diagnostic apparatus has a camera control section 10 and image processing section 11. The camera control section 10 controls imaging by the fluoroscopic camera head 8 and radiographic camera head 9. The image processing section 11 performs a prescribed image process such as a video process on the fluoroscopic image signal generated by the fluoroscopic camera head 8 and the radiographic image signal generated by the radiographic camera head 9, and supplies these signals to a monitor unit 12.

Figure 3A:
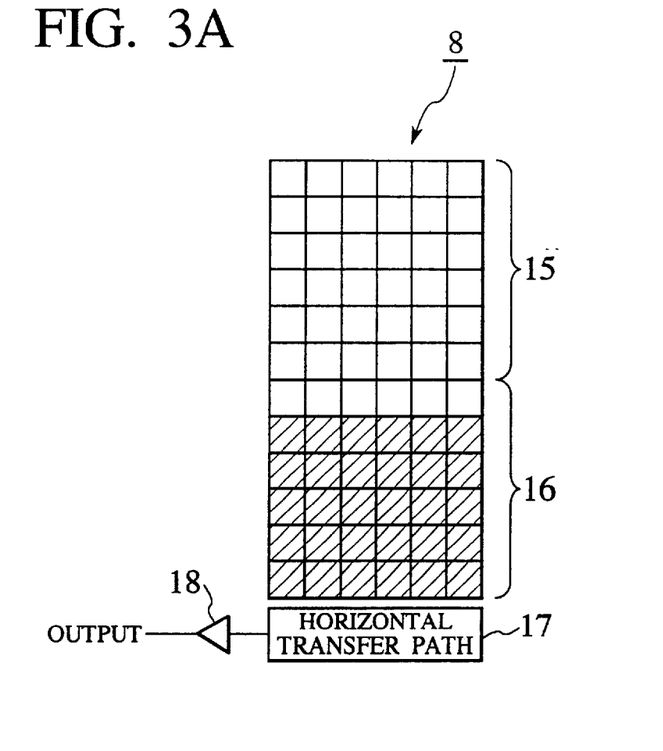
FIGS. 3A and 3B are drawings showing respectively constitutions of FTCCD provided to a fluoroscopic camera head and FFTCCD provided to a radiographic camera head.

A frame transfer CCD image sensor (FTCCD) shown in FIG. 3A is provided to the radiographic camera head 8. The FTCCD is composed of an imaging section 15 where receiving elements (pixels) are arranged in a matrix pattern, a memory section 16 as a light shielding area for storing electric charges transferred vertically at high speed from the imaging section 15, a horizontal transfer path 17 for horizontally transferring the electric charges stored in the memory section 16 as a fluoroscopic image signal, and an amplifier 18 for amplifying the fluoroscopic image signal transferred horizontally by prescribed gain so as to output the amplified fluoroscopic image signal. The fluoroscopic camera head 8 composed of the FTCCD is provided for imaging a moving picture, and it is used only at the time of "fluoroscopy".

Here, in the fluoroscopic camera head 8, besides the FTCCD, an interline transfer CCD image sensor (ITCCD) or frame interline transfer CCD image sensor (FITCCD) may be used.

Figure 3B:
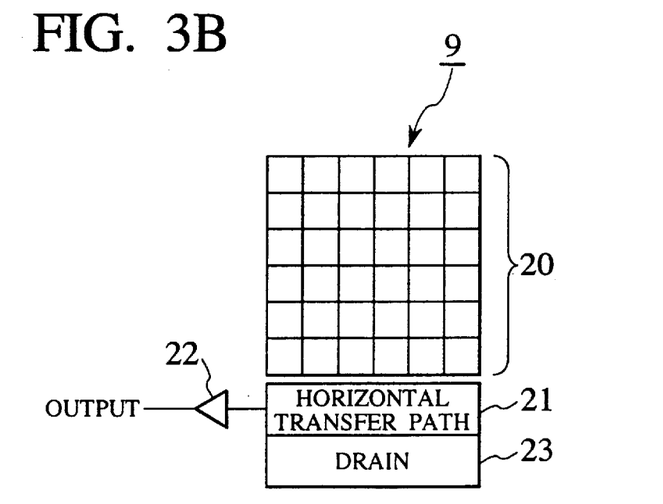

A full-frame CCD image sensor (FFTCCD) shown in FIG. 3B is provided to the radiographic camera head 9. The memory section 16 is not provided to the FFTCCD unlike FTCCD, and is composed of an imaging section 20 in which the pixels arranged in the vertical direction serve also as a vertical transfer path, a horizontal transfer path 21 for horizontally transferring electric charges vertically transferred from the imaging section 20 as a radiographic image signal, an amplifier 22 for amplifying the radiographic image signal horizontally transferred by prescribed gain to output the amplified radiographic image signal, and a drain 23 for sweeping away unnecessary electric charges in a dark current clear period, etc., mentioned later.

The FFTCCD does not have the memory section 16 unlike FTCCD. In the FFTCCD, by making use of that the pixels arranged in the vertical direction serve also as the vertical transfer path for electric charges, the pixel size is increased, and the number of pixels is increased. As a result, high-resolution image can be radiographed. Even when the pixel size is increased and the number of pixels is increased in such a manner, the whole chip size does not become large because the FFTCCD has the aforementioned constitutional characteristics, and thus the cost does not become high. The radiographic camera head 9 composed of the FFTCCD is provided for imaging a still picture, so it is used only at the time of "radiography".

The following describes an operation of the X-ray diagnostic apparatus according to the embodiments having such a constitution.

In the case where the X-ray diagnostic apparatus is used, in a general method, first, an affected part is observed through "fluoroscopy" and the proper time for radiography is chosen, and "radiography" is specified in desired timing so that a radiographic image is obtained. When the description proceeds according this order, an operator first specifies "fluoroscopy".

When the "fluoroscopy" is specified, the X-ray control section 1 supplies an irradiation request signal to the image processing section 11. When the irradiation request signal is supplied, the image processing section 11 synchronizes this signal with a camera VD as an internal clock in the camera control section 10 to form an irradiation start signal, and transmits back the irradiation start signal to the X-ray control section 1.

When the irradiation start signal is supplied, the X-ray control section 1 controls driving of the X-ray tube 2 so that the X-ray tube 2 irradiates a little amount of X rays successively, and controls rotation of the rotating mirrors 6 in the optical path changing section 5 so that an X-ray image enters the fluoroscopic camera head 8. As a result, an examinee is irradiated with the X rays and the X-ray image is formed.

The image intensifier 4 captures the X-ray image and converts it into an X-ray image of a visible light. This X-ray image of a visible light enters the optical path changing section 5, and is reflected, for example, at an angle of 90° from the rotating mirrors 6 to enter the fluoroscopic camera head 8.

The fluoroscopic camera head 8 images the X-ray image of a visible light to form a fluoroscopic image signal which is an electric signal, and supplies this signal to the image processing section 11.

Figure 4:
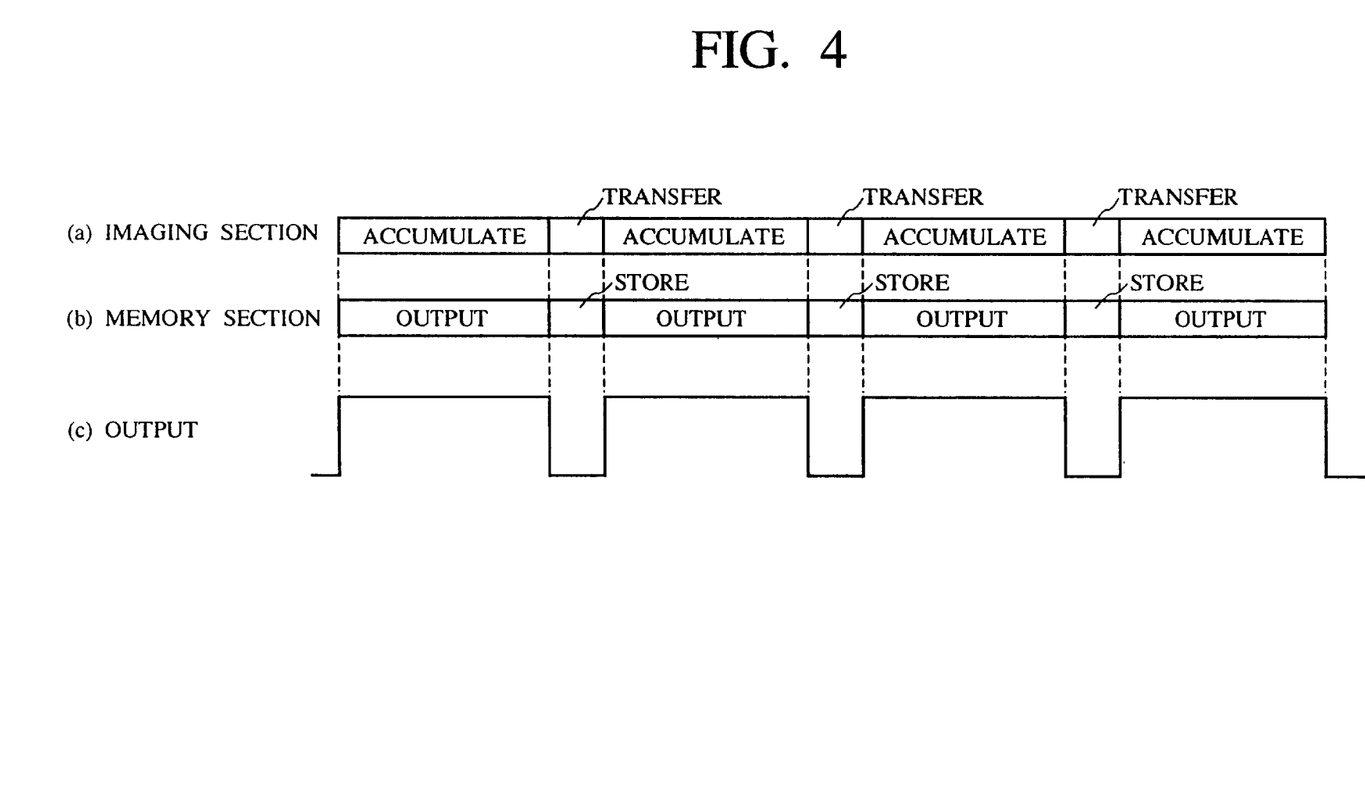
FIG. 4 is a time chart for explaining an operation of fluoroscopy in the X-ray diagnostic apparatus according to embodiment.

More specifically, the fluoroscopic camera head 8 is composed of the FTCCD as shown in FIG. 3A, and when the X-ray image of a visible light enters there, as shown in (a) of FIG. 4, (each pixel of) the imaging section 15 accumulates electric charges according to the amount of the visible light for constant time, and the accumulated electric charges are vertically transmitted at high speed to the memory section 16 according to frame alignment in the vertical interval time code.

When all the electric charges are vertically transferred at high speed, the memory section 16 temporarily stores them thereinto as shown in (b) of FIG. 4, and vertically transfers them every one horizontal line to the horizontal transfer path 17, and the horizontal transfer path 17 horizontally transfers them based on a driving clock of a frame rate supplied from the camera control section 10. The horizontally transferred electric charges are amplified by a prescribed gain in the amplifier 18, and as shown in (c) of FIG. 4, the amplified electric charges are supplied to the image processing section 11 shown in FIG. 2 as a fluoroscopic image signal.

During "fluoroscopy", the camera control section 10 controls the imaging section 15 so that the accumulation and high-speed vertical transfer are repeated, and controls the memory section 16 and horizontal transfer path 17 so that the storage and outputting of the electric charges vertically transferred at high speed are repeated.

Since the FTCCD provided with the fluoroscopy camera head 8 has the memory section 16, while the electric charges are being accumulated in the imaging section 15, the electric charges stored in the memory section 16 can be read, and a moving picture can be imaged following the X rays irradiated successively.

When the fluoroscopic image signal formed in such a manner is supplied, the image processing section 11 performs a prescribed image process on the fluoroscopic image signal and supplies it to the monitor unit 12. As a result, a moving picture of the fluoroscopic image can be displayed on the monitor unit 12.

Next, the operator observes the fluoroscopic image displayed on the monitor unit 12 and at the same time chooses the proper time, etc., and specifies "radiography" in desired timing.

When the "radiography" is specified, the X-ray control section 1 supplies an irradiation request signal to the image processing section 11, and when an irradiation start signal which synchronizes with the camera VD of the camera control section 10 is transmitted back from the image processing section 11 to the X-ray control section 1, the X-ray control section 1 controls the driving of the X-ray tube 1 so that it irradiates great amounts of X rays at one shot. Moreover, the X-ray control section 1 also controls the rotation of the rotating mirrors 6 in the optical path changing section 5 so that the X-ray image enters the radiographic camera head 9.

The image intensifier 4 captures the X-ray image formed by the irradiation of the X rays at one shot and converts it into the X-ray image of a visible light. The X-ray image of a visible light enters the optical path changing section 5 and is reflected from the rotating mirrors 6 at 90°, for example, to enter the radiographic camera head 9.

The radiographic camera head 9 forms a radiographic image signal which is an electric signal by imaging the X-ray image of a visible light and supplies this signal to the image processing section 11.

More specifically, the radiographic camera head 9 is composed of FFTCCD as shown in FIG. 3B, and just before the X-ray image of a visible light enters (just before the irradiation of X rays is started), the excessive electric charges accumulated in the imaging section 20 are vertically transferred at high speed to the drain 23 through the horizontal transfer path 21 to sweep away them (the operation in the dark current clear period, mentioned later). When the X-ray image of a visible light enters, (each pixel of) the imaging section 20 accumulates electric charges according to an amount of the visible light for constant time, and after the constant time passes, the electric charges accumulated in each pixel are vertically transferred to the horizontal transfer path 21 per horizontal line, and they are horizontally transferred based on a driving clock of the frame rate from the camera control section 10. The electric charges horizontally transferred are amplified by a prescribed gain in the amplifier 22, and the amplified electric charges are supplied to the image processing section 11 shown in FIG. 2 as a radiographic image signal.

Every time "radiography" is specified, the camera control section 10 controls the imaging section 20 and drain 23 so that the dark current clear operation, accumulation of electric charges and vertical transfer are carried out, and also controls the horizontal transfer path 21 so that the vertically transferred electric charges are outputted (horizontal transfer).

Since the FFTCCD provided to the radiographic camera head 9 does not have the memory section 16 unlike FTCCD, an image signal cannot be outputted during the accumulation of electric charges, it is difficult to image a moving picture by X rays irradiated successively, but since X rays are irradiated at one shot at the time of "radiography", a still picture (radiographic image) obtained by "radiography", can be imaged without any difficulty in its constitution.

In addition, the FFTCCD provided to the radiographic camera head 9 does not have the memory section 16 as mentioned above, and each pixel arranged in the vertical direction serves also as the vertical transfer path for electric charges. This makes the pixel size large, and a number of pixels is increased. For this reason, a high-definition radiographic image with excellent S/N characteristic (the S/N characteristic depends on the pixel size) can be formed at high space sampling frequency, namely, with high resolution, and at low costs.

The image processing section 11 performs a prescribed image process on the supplied radiographic image signal and supplies it to the monitor unit 12 as well as stores it into the data base. As a result, the high-definition radiographic image (still picture) which is not inferior to that in an X film can be displayed on the monitor unit 12, and the radiographic image is stored in the data base to be able to contribute to references.

In addition, since the radiographic image is displayed on the monitor unit 12, the radiographic image can be checked immediately after the radiography without developing it unlike an X film, and even if the radiography becomes a failure, radiography can be carried out again immediately. Moreover, since the radiographic image can be stored electrically in the data base, its reference becomes easy, thereby producing an effect that there is no difficulty in a storage place for the radiographic images.

Figure 5:
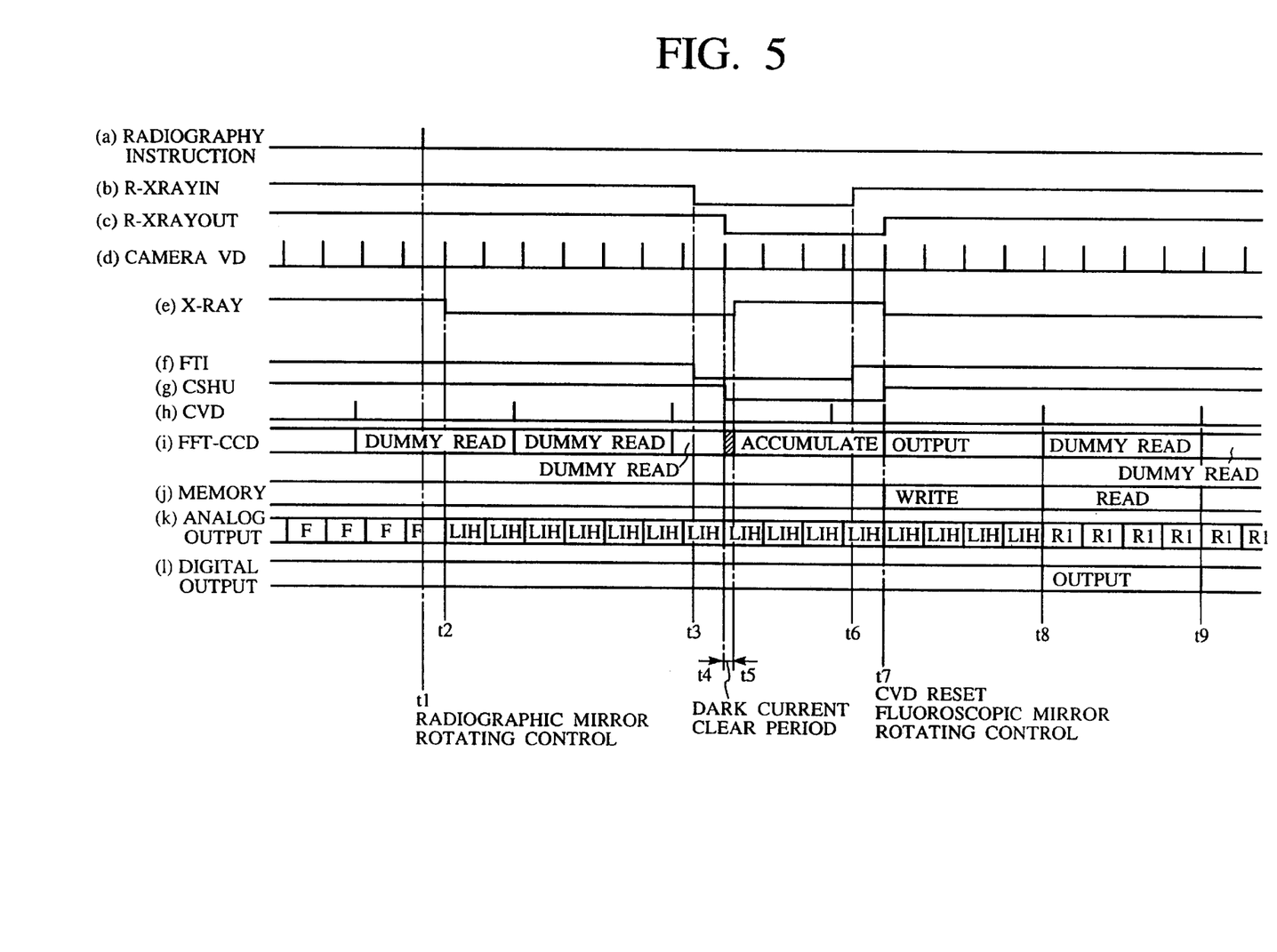
FIG. 5 is a time chart for explaining an operation of radiography in the X-ray diagnostic apparatus according to embodiment.

The following details the radiographic operation at the time of the "radiography" on reference with the time chart shown in FIG. 5.

A camera VD signal which is a clock with width of 33 msec, for example, shown in (d) of FIG. 5 is supplied from the camera control section 10 to the image processing section 11.

First, if "radiography" is specified by an operator at time t1 shown in (a) of FIG. 5, as shown in (k) of FIG. 5, the image processing section 11 displays the last image of fluoroscopic images (F), which have been displayed as moving pictures (the fluoroscopic image displayed when "radiography" is specified), as a still picture (LIH: last image hold).

In addition, if "radiography" is specified by an operator at time t1 shown in (a) of FIG. 5, the X-ray control section 1 controls rotation of the rotating mirrors 6 in the optical path changing section 5 so that an X-ray image enters the radiographic camera head 9. Moreover, after the rotation of the rotating mirrors 6 in the optical path changing section 5 is controlled, as shown in time t3 to time t6 in (b) of FIG. 5, an irradiation request signal (R-XRAYIN) which is a pulse of a low level for prescribed time is supplied to the image processing section 11.

Here, FIG. 5 shows that the rotation of the rotating mirrors 6 in the optical path changing section 5 is controlled during seven camera VD period, but this is one example and it is not limited to seven camera VD period, so this period can be set freely according to design.

When the irradiation request signal is supplied, as sown in time t4 to time t7 in (c) of FIG. 5, the image processing section 11 synchronizes this signal with a camera VD signal to form an irradiation start signal, and transmits back this signal to the X-ray control section 1.

When the X-ray control section 1 detects a radiography instruction shown in time t1 in (a) of FIG. 5, as shown in time t2 in (e) of FIG. 5, the X-ray control section 1 controls the X-ray tube 1 to stop X rays for fluoroscopy which have been irradiated. When the X-ray control section 1 detects fall of the irradiation start signal shown in time t4 in (c) of FIG. 5, after the dark current clear period, mentioned later, passes, the X-ray control section 1 controls driving of the X-ray tube 1 so that the X-ray tube 1 irradiates great amounts of X rays for constant time shown in time t5 to time t7 in (e) of FIG. 5.

As a result, an X-ray image for a radiographic image is formed and is reflected from the rotating mirrors 6 to enter the radiographic camera head 9.

Meanwhile, when the image processing section 11 detects fall of the irradiation request signal from the X-ray control section 1, shown in time t3 in (b) of FIG. 5, as shown in time t3 to time t6 in (f) of FIG. 5, the FTI signal, which has been supplied to the camera control section 10 as a high-level signal, becomes low level for four camera VD periods.

When the low-level FTI signal is supplied, the camera control section 10 synchronizes this signal with the camera VD signal as shown in time t4 to time t7 in (g) of FIG. 5 to form a CSHU signal, and resets a CCD driving pulse (CVD) supplied to the FFTCCD of the radiographic camera head 9 as shown in time t7 in (h) of FIG. 5 in timing that rise of the CSHU signal shown in time t7 in (g) of FIG. 5 is detected. After reset, the reset CCD driving pulse is supplied to the FFTCCD per four camera VD periods, for example, as shown in time t7, time t8, time t9 . . . in (h) of FIG. 5.

The FFTCCD of the radiographic camera head 9 performs dummy reading of the electric charges accumulated in the imaging section 20 until time t4 in (i) of FIG. 5, namely, until it detects fall of the CSHU signal from the camera control section 10, but when fall of the CSHU signal is detected, the FFTCCD vertically transfers unnecessary electric charges accumulated in the imaging section 20 to the drain 23 at high speed during time from the fall to starting of irradiation of X rays (time t5 in (e) of FIG. 5), namely, during short time shown from time t4 to time t5 in (i) of FIG. 5, and sweeps away the unnecessary electric charges, and clears dark current (dark current clear period shown by slanted lines in (i) of FIG. 5).

When the dark current clear operation is ended, the FFTCCD accumulates electric charges for a period that X rays are irradiated as shown in time t5 to time t7 in (i) of FIG. 5. Then, based on the reset CCD driving pulse shown in (h) of FIG. 5, the electric charges are read by the time a next CCD driving pulse is supplied (during four camera VD periods) as shown in time t7 to time t8 in (i) of FIG. 5, and these electric charges are supplied as radiographic image signals to the image memory provided into the camera control section 10.

As shown in time t7 to time t8 in (j) of FIG. 5, the camera control section 10 temporarily stores the radiographic image signals supplied from the FFTCCD into the image memory, and reads them for four camera VD periods shown in time t8 to time t9 in (j) of FIG. 5 to supply the signals to the image processing section 11.

The image processing section 11 performs a prescribed image processing process on the radiographic image signals read from the image memory to supply them to the monitor image 12. As a result, after the radiographic image signals are read from the image memory, a display image on the monitor unit 12 which has been a still picture of a fluoroscopic image from the timing that radiography is specified can be a radiographic image (R1) as shown in and after time t8 in (k) of FIG. 5. When an operator sees the radiographic image displayed immediately after the radiography, the operator can know a success or a failure of the radiography immediately.

In addition, the radiographic image signals read from the frame memory as digital signals are supplied to and stored in the data base as shown in (1) of FIG. 5. As a result, a radiographic image can be stored electronically, and it can be referred to easily by reproducing it.

Here, when the camera control section 10 detects rise of the CSHU signal shown in time t7 in (g) of FIG. 5 (the irradiation of X rays for the radiographic image is ended), the camera control section 10 controls rotation of the rotating mirrors 6 in the optical path changing section 5 so that an X-ray image enters the fluoroscopic camera head 8, and waits for the instruction of "fluoroscopy".

Figure 6:
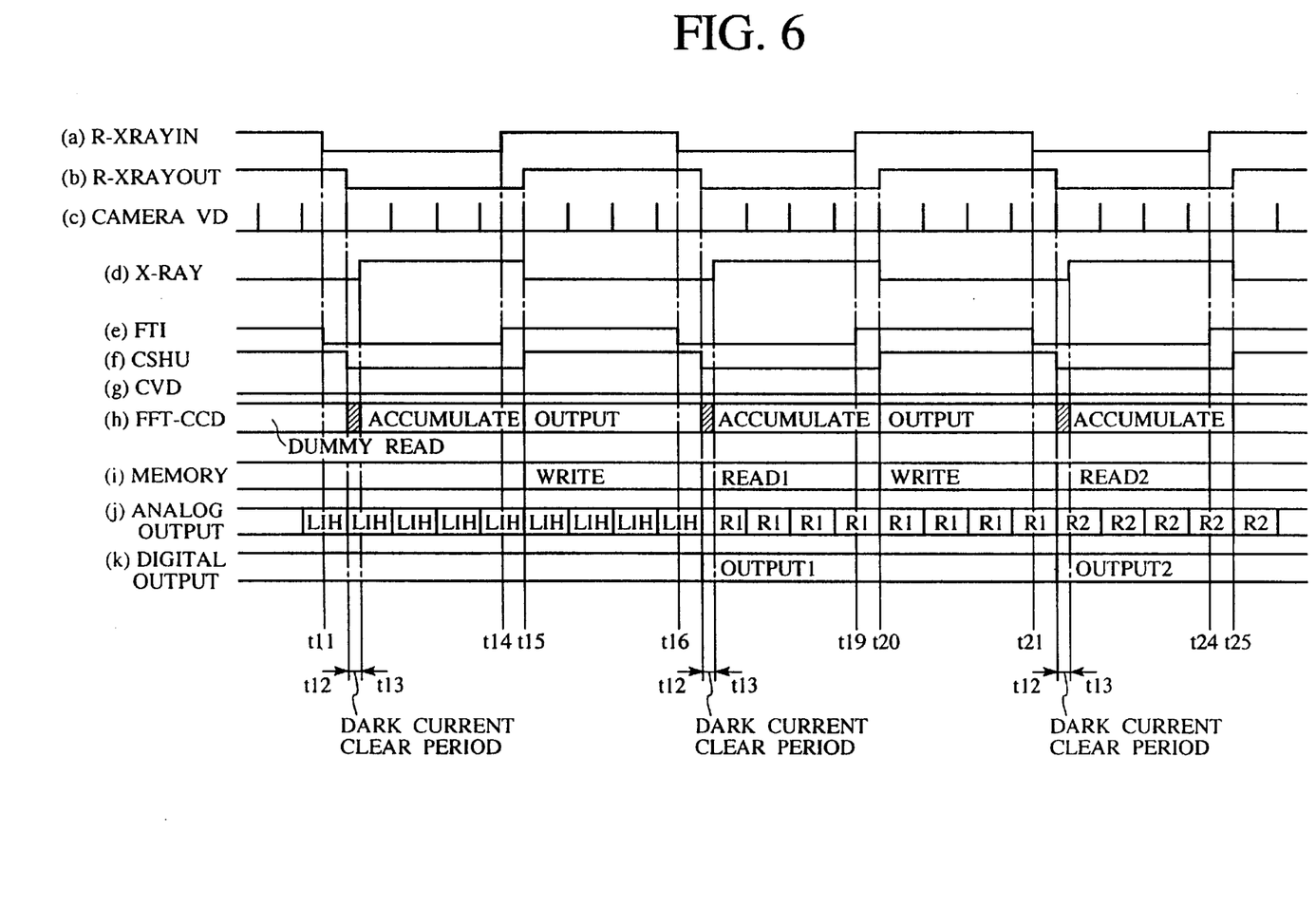
FIG. 6 is a time chart for explaining an operation of successive radiography in the X-ray diagnostic apparatus according to embodiment.

Since the X-ray diagnostic apparatus can carry out such "radiography" successively per constant time, when "successive radiography" is specified by an operator, the X-ray control section 1 supplies an irradiation request signal to the image processing section 11 successively per constant time as shown in time t11 to time t14, time t16 to time t19, t21 to time t24 ... in (a) of FIG. 6.

When the image processing section 11 synchronizes the irradiation request signal with a camera VD signal shown in (c) of FIG. 6, it forms an irradiation start signal shown in time t12 to time t15, time t17 to time t20, time t22 to time t25 ... in (b) of FIG. 6 and supplies this signal to the X-ray control section 1.

Every time the irradiation start signal is supplied, the X-ray control section 1 controls driving of the X-ray tube 1 so that the X-ray tube 1 irradiates great amounts of X rays for constant time shown in time t13 to time t15, time t18 to time t20, time t23 to time t25 ... in (d) of FIG. 6 in the timing at which the dark current clear period passes. As a result, X-ray images for the radiographic images are formed successively, and enters the radiographic camera head 9 through the rotating mirrors 6.

Meanwhile, when detecting rise of the irradiation request signal shown in time t11, time t16, time t21 ... in (a) of FIG. 6, the image processing section 11 sets an FTI signal, which has been supplied to the camera control section 10 at a high level, to a low level for four camera VD periods as shown in time t11, time t16, time t21 ... in (e) of FIG. 6.

When this low-level FTI signal is supplied, the camera control head 10 synchronizes this signal with the camera VD signal as shown in time t12 to time t15, time t17 to time t20, time t22 to time t25 ... in (f) of FIG. 6 to form a CSHU signal, and resets a CCD driving pulse (CVD), which has been supplied to the FFTCCD of the radiographic camera head 9 as shown in time t15 in (g) of FIG. 6, in the time at which rise of the CSHU signal shown in time t15 in (f) of FIG. 6 is first detected. After being reset, this CCD driving pulse is supplied to the FFTCCD per four camera VD periods, for example, as shown in time t15, time t17, time t20, time t22 ... in (g) of FIG. 6.

When detecting fall of the CSHU signal from the camera control section 10, the FFTCCD of the radiographic camera head 9 vertically transfers unnecessary electric charges accumulated in the imaging section 20 to the drain 23 at high speed to sweep them away during the time from the fall to starting of the irradiation of X rays, namely, during short periods shown in time t12 to t13, time t17 to time t18, time t22 to time t23 ... in (h) of FIG. 6, and clears dark current (dark current clear period shown by slanted lines in (h) of FIG. 6).

When the dark current clear operation is ended, the FFTCCD accumulates electric charges for time at which the X rays are irradiated as shown in time tl3 to time t15, time t18 to time t20, time t23 to time t25 ... in (h) of FIG. 6. The electric charges are read by the time next dark current clear period is supplied (four camera VD periods) as shown in time t15 to t17, time t20 to time t22 ... in (h) of FIG. 6 based on the reset CCD driving pulse shown in (g) of FIG. 6, and are supplied as the radiographic image signal to the image memory provided into the camera control section 10.

As shown in time t15 to time t17, time t20 to time t22 ... in (i) of FIG. 6, the camera control section 10 temporarily stores the radiographic image signal supplied from the FFTCCD into the image memory, and reads this signal successively during four camera VD periods shown in time t17 to time t20 (first radiographic image), time t22 to time t25 (second radiographic image). .. in (i) of FIG. 6 to supply the signal to the image processing section 11.

When "successive radiography" is specified, as shown in (j) of FIG. 6, the image processing section 11 displays a still picture (LIH) on the monitor by last image hold, but when the first radiographic image (R1) is supplied, the image processing section 11 changes the display from the still picture to the first radiographic image to display it on the monitor, and when the second radiographic image (R2) is supplied, the image processing section 11 changes display from the first radiographic image to the second radiographic image to display it on the monitor. Namely, every time the successive radiography is ended, the image processing section 11 changes the respective radiographic images to display them.

As a result, while seeing the respective radiographic images displayed successively, the operator can identify a successful or failed of radiography immediately.

In addition, the respective radiographic image signals read from the image memory, as shown in (k) of FIG. 6, are supplied to and stored in the data base as digital signals (OUTPUT1, OUTPUT2). As a result, the respective radiographic images can be stored electrically, and they can be referred to easily by reproducing them.

As mentioned above, the X-ray diagnostic apparatus has the fluoroscopic camera head 8 with FTCCD used for fluoroscopy and the radiographic camera head 9 with FFTCCD used for radiography, and these camera heads are used by selectively switching according to fluoroscopy and radiography. As a result, both moving pictures (fluoroscopy images) and still pictures (radiographic images) with high resolution can be obtained by using solid imaging means. Moreover, since only the radiographic camera head 9 having FFTCCD and the optical path changing section 5 are added to the existing X-ray diagnostic apparatus, the constitution is simple and the cost is low.

In addition, at the time of "radiography", the image processing section 11 forms the irradiation start signal ((b) of FIG. 5) which is synchronized with an internal clock (camera VD: (d) of FIG. 5) of the camera control section 10, and the X-ray control section 1 irradiates X rays for about four camera VD periods, for example, based on the irradiation start signal, and the camera control section 10 controls the radiographic camera head 9 so that radiography (accumulation of electric charges) is carried out for four camera VD periods as one operational period which is synchronized with the camera VD signal. In other words, X rays are irradiated and radiography is carried out synchronously with a camera VD signal whose period is shorter than and which is synchronized with the one operational period (four camera VD) of the radiographic camera head 9. For this reason, the radiography can be carried out in radiographic timing which is substantially desired by the operator.

In addition, the FFTCCD of the radiographic camera head 9 sweeps away unnecessary electric charges to the drain 23 (dark current clear) just before the irradiation of X rays are started, and then electric charges are accumulated synchronously with the camera VD signal. For this reason, the radiographic image signal can be transmitted easily between equipments in the system which operates synchronously (radiographic camera head 9, camera control section 10 and image processing section 11) without accumulation of electric charges due to unnecessary dark current.

In addition, since the FFTCCD of the radiographic camera head 9 accumulates electric charges in a frame where X rays are irradiated and reads the accumulated electric charges in a frame after the irradiation of X rays is ended to output them, a radiographic image without a false image such as smear can be obtained.

Figure 7A:
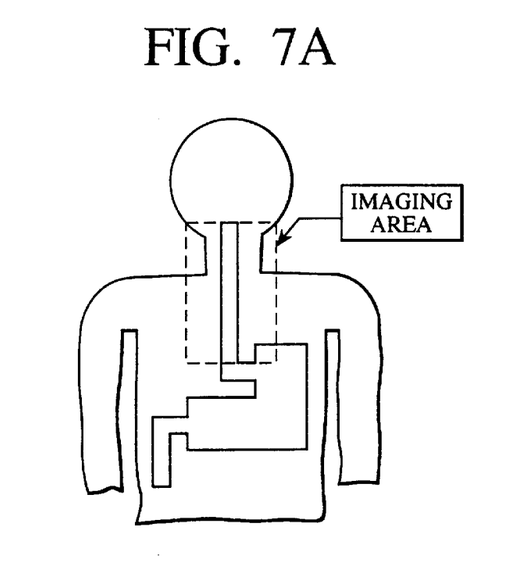
FIG. 7A is a drawing showing a radiographic range in the case where test for the upper digestive organ using contrast media is performed.

In the case where an upper digestive organ (esophagus portion) shown in FIG. 7A is put to the test using contrast media, etc., since an image other than that of the esophagus is not necessary, it is not preferable that the portions other than the esophagus is irradiated with X rays. Moreover, it is necessary to obtain some radiographic images until barium which was drunk by an examinee reaches the stomach (while barium passes through the esophagus), radiography in early period is required, so it is necessary to raise the frame rate (radiographic period).

Therefore, as shown in FIG. 2, the X-ray diagnostic apparatus is provided with the X-ray shielding section 3 for shielding unnecessary X rays of the X rays irradiated from the X-ray tube 1. Moreover, the FFTCCD of the radiographic camera head 9 is provided with it being rotated through an angle of 90° so that the horizontal scanning direction coincides with a direction of the height of the examinee (body-axial direction).

Figure 7B:
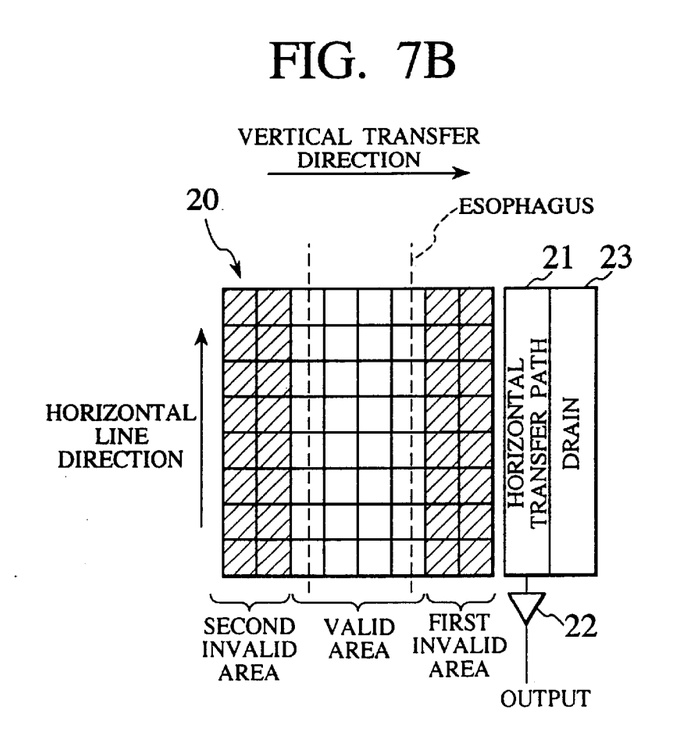
FIG. 7B is a drawing for explaining FFTCCD of a radiographic camera head whose position is adjusted so that a radiographic image rotated through an angle of 90° can be obtained.

Namely, the FFTCCD is provided with it being rotated through an angle of 90° so that when an X-ray image of the examinee's esophagus enters, as shown in FIG. 7B, horizontal lines composed of pixels provided in the horizontal transfer direction is along the esophagus (the direction of the horizontal lines are the direction of the esophagus (the direction from the mouth to the stomach)).

Such a radiographic operation of the X-ray diagnostic apparatus is described by illustrating the test of the upper digestive organ using contrast media. First, the operator specifies the test of the upper digestive organ using contrast media. When this is specified, the X-ray shielding section 3 controls an aperture width of the aperture through which X rays passes so that only the esophagus of an examinee is irradiated with the X rays.

More specifically, as shown in FIG. 7B, when the number of the horizontal lines of FFTCCD is 8, for example, the X-ray shielding section 3 controls the aperture width of the aperture so that portions shown by slanted lines corresponding to two horizontal lines (portions in the circumference of the esophagus) located on the right and left sides of FFTCCD are not irradiated with X rays.

As a result, only the portion (the esophagus) corresponding to four horizontal lines which are central imaging areas of the FFTCCD can be irradiated with X rays, so only the portion which really requires a radiographic image can be irradiated with X rays. Therefore, unnecessary exposure of an examinee can be reduced.

Next, in the case where a radiographic image which was imaged by adjusting irradiation areas in such a manner is read, the camera control section 10 first vertically transfers electric charges accumulated in the first invalid area corresponding to two horizontal lines in the right side of FFTCCD at high speed to sweep away them to the drain 23 through the horizontal transfer path 21.

Next, the camera control section 10 vertically transfers electric charges accumulated in a valid area for central four horizontal lines corresponding to the irradiated area with X rays to the horizontal transfer path 21 per line, and outputs them as the radiographic image signal from the horizontal transfer path 21 and ends the reading of the radiographic image.

Namely, at the stage that the reading in the central area (central four horizontal lines) is ended, electric charges in the second invalid area are vertically transferred to the first invalid area, but the electric charges in the second invalid area which were vertically transferred to the first invalid area are unnecessary. For this reason, the camera control section 10 ends the reading of the radiographic image at the stage that the reading of the central area (central four horizontal lines) is ended, and the unnecessary electric charges in the second invalid area, which were vertically transferred to the first invalid area, as well as the unnecessary electric charges in the first invalid area are swept away to the drain area when a radiographic image is read at next radiography.

Figure 8:
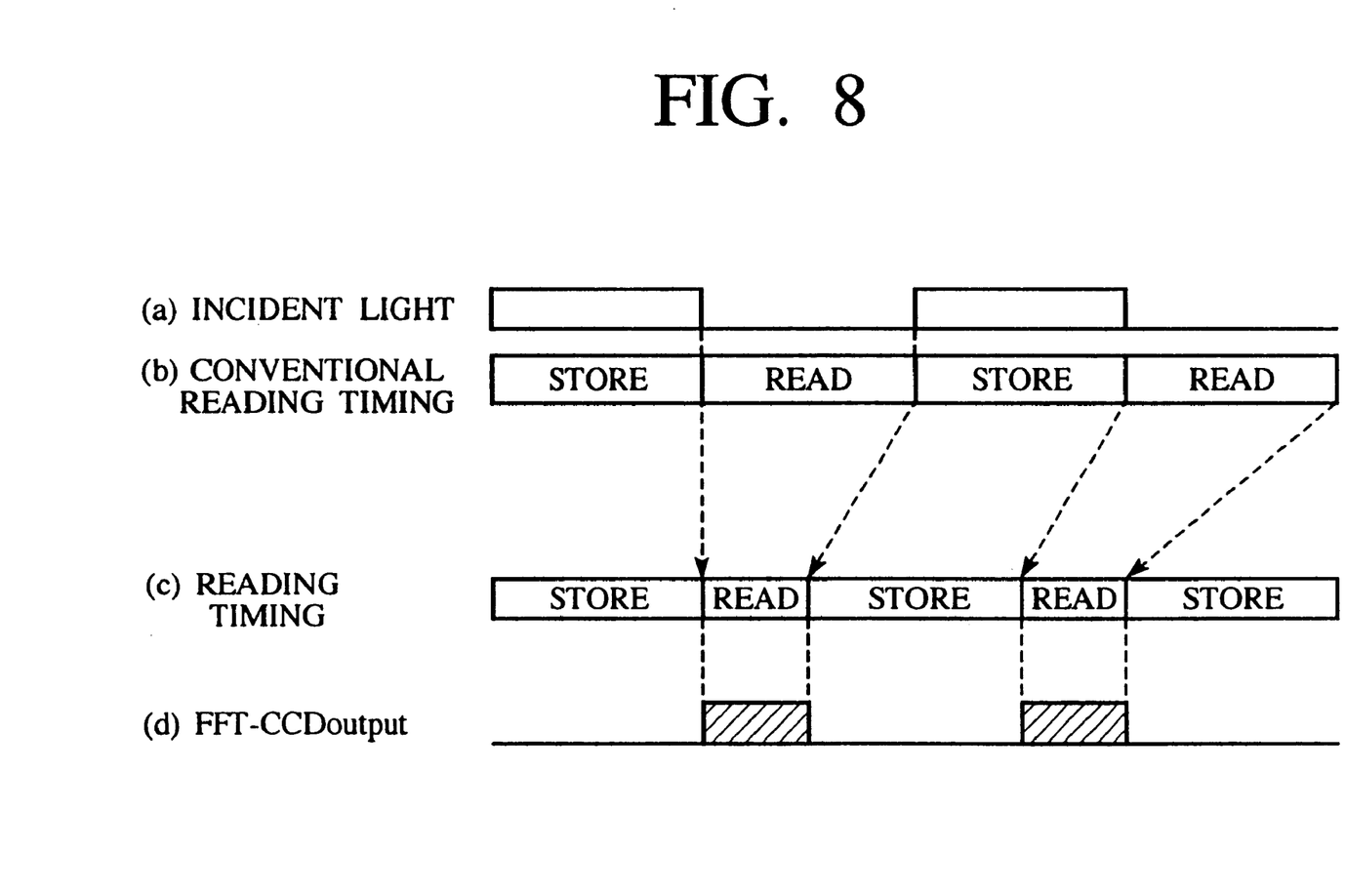
FIG. 8 is a time chart for explaining a reading control operation for heightening a speed of a frame rate in the FFTCCD whose position was adjusted.

As a result, as shown in (a) through (d) of FIG. 8, the whole reading time can be shortened to "sweeping-away time of the unnecessary electric charges in the first invalid area+reading time of the valid electric charges in the central area", and the frame rate can be improved. Therefore, the radiography in early period can be realized without driving the FFTCCD at high speed without any difficulty, and thus some radiographic images can be obtained until barium drunk by an examinee reaches the stomach.

In addition, in the case where the FFTCCD whose position is controlled is not provided with the drain 23, its driving may be controlled in the following manner.

Namely, in this case, when electric charges are accumulated in the FFTCCD whose position is controlled, the camera control section 10 vertically transfers the unnecessary electric charges in the first invalid area to the horizontal transfer path 21 at high speed to add the unnecessary electric charges for two lines, and outputs them collectively as electric charges for one line. As a result, the unnecessary electric charges in the first invalid area can be wept away for one horizontal scanning period. After the valid electric charges in the valid area are outputted successively, the unnecessary electric charges in the second invalid area are vertically transferred to the horizontal transfer path 21 at high speed similarly to the unnecessary electric charges in the first invalid area to add them for two lines, and outputs them collectively as electric charges for one line.

As a result, the unnecessary electric charges in the respective invalid areas can be read for two horizontal scanning periods, and the whole reading time can be shortened to "reading time of valid electric charges for four lines+reading time of unnecessary electric charges for two lines". Therefore, the frame rate can be improved about 1.3 times as much as the usual cases.

Here, by adding the unnecessary electric charges in the horizontal transfer path 21, in the case where electric charges overflows in the horizontal transfer path 21, the unnecessary electric charges in the respective lines may be added in several times within the limits that the electric charges do not overflow.

Next, the radiographic image signal, which was read from the FFTCCD in such a manner, is temporarily stored in the image memory provided into the camera control section 10 in the order of the horizontal scanning. The image processing section 11 controls the reading so that the radiographic image signal stored in the image memory is read in a direction which intersects perpendicularly to the horizontal scanning direction, and supplies it to the monitor unit 12.

In addition, in the medical equipment, since it is determined customarily that an radiographic image is display so that a direction from the top portion to the bottom portion of the monitor display screen coincides with a direction from the head to the foot of an examinee in the image to be displayed, when the radiographic image signal is read from the image memory, the image processing section 11 controls the reading so that the top portion of the displayed image (image in the examinee's head direction) is displayed on the top portion of the monitor display screen according to the custom.

The reading from the image memory can be controlled easily only by controlling a read address of the image memory.

As a result, the radiographic image of the esophagus portion in the direction from the examinee's head to foot can be displayed, and thus the test of the upper digestive organ can be put to the test using contrast media in the direction from the top portion to the bottom portion of the monitor unit 12.

Here, the above explanation referred to the case of the test of the upper digestive organ using contrast media, but also in the case where another tests are made, as mentioned above, the image processing section 11 reads radiographic image signals, which were stored in the image memory in the order of the horizontal scanning by the FFTCCD which was rotated through an angle of 90°, in the direction intersecting perpendicularly to the horizontal scanning direction to supply the signals to the monitor unit 12.

Finally, in the aforementioned description of embodiment, the radiographic image displayed on the monitor unit 12 is displayed until "fluoroscopy" (or "radiography") is specified next, but after a radiographic image is displayed for prescribed time (for example, momentarily), the display may be switched to a fluoroscopic image where the last image is held.

In addition, the pulse interval of the camera VD signal is 33 msec, and the CCD driving pulse after resetting is four camera VD periods, namely, the description referred to concrete numeric values, but these are examples given for easy understanding of the present invention. For this reason, the present invention is not limited to these numeric values, so it is needless to say that changes are possible according to designs without departing from the spirit of essential characteristics of the present invention.

The X-ray diagnostic apparatus of the present invention can obtain a satisfactory moving picture (fluoroscopic image) at the time of fluoroscopy, and a high-definition still picture (radiographic image) at the time of radiography. For this reason, efficiency of tests such as the test of digestive organs, and accuracy in diagnosis can be improved.

It should be understood that many modifications and adaptations of the invention will become apparent to those skilled in the art and it is intended to encompass such obvious modifications and changes in the scope of the claims appended hereto.

What is claimed is:

1. An X-ray diagnostic apparatus, comprising:

X-ray generating means for irradiating an examinee with X rays;

X-ray generation control means for controlling said X-ray generating means to irradiate X rays successively at a time of fluoroscopy and for controlling said X-ray generating means to irradiate greater amounts of X rays at a time of radiography other than at the time of fluoroscopy;

X-ray/visible-light converting means for converting an X-ray image into visible light;

first solid state imaging means for receiving the X-ray image of visible light at the time of the fluoroscopy to form a fluoroscopic image;

second solid state imaging means for receiving the X-ray image of visible light at the time of the radiography to form a radiographic image after sweeping away electric charges previously stored therein due to a dark current, wherein said second solid state imaging means is a solid state image sensor including a two dimensional array having horizontal and vertical pixels, and is configured to directly and vertically transfer electric charges accumulated in an imaging section thereof to a horizontal transfer path, and has a greater number of pixels than the number of pixels of said first solid state imaging means;

visible light directing means for selectively directing an optical path for the X-ray image of visible light from said X-ray/visible-light converting means to the first solid state imaging means or to the second solid state imaging means; and X-ray shielding means for controlling the width of an aperture window of said X-ray generating means to be variable in a direction perpendicular to the horizontal transfer path of said second solid state imaging means in order to partially shield the X rays irradiated therefrom such that selected portions of the examinee are shielded from being irradiated with the X-rays.

2. The X-ray diagnostic apparatus according to claim 1, further comprising driving control means for controlling said second solid state imaging means to read and sweep the away electric charges previously stored therein due to the dark current and corresponding to the shielded X-rays to a drain area via the horizontal transfer path, and to read and output as a radiographic image signal electric charges which correspond to unshielded X-rays from the horizontal transfer path.

3. The X-ray diagnostic apparatus according to claim 2, wherein said driving control means controls said second solid state imaging means to stop reading electric charges in a frame upon completion of reading the electric charges which correspond to unshielded X-rays, and before reading electric charges in a next frame, to sweep away electric charges due to dark current and corresponding to the shielded X-rays in the frame together with electric charges due to dark current and corresponding to the shielded X-rays in the next frame to the drain area.

4. The X-ray diagnostic apparatus according to claim 1, further comprising driving control means for controlling said second solid state imaging means to read the electric charges in each horizontal line due to the dark current and corresponding to the shielded X-rays at high speed, to add all the electric charges which correspond to the shielded X-rays on the horizontal transfer path, and then to sweep away the added electric charges which correspond to the shielded X-rays to a drain area via the horizontal transfer path, while sequentially reading and outputting electric charges in each horizontal line which correspond to unshielded X-rays.

5. The X-ray diagnostic apparatus according to claim 1, further comprising driving control means for controlling said second solid state imaging means to sweep away electric charges previously stored in said second solid state imaging means prior to receiving X-ray image of visible light.

6. An X-ray diagnostic apparatus, comprising:

X-ray generating means for irradiating an examinee with X rays;

X-ray generation control means for controlling said X-ray generating means to irradiate X-rays successively at a time of fluoroscopy and for controlling said X-ray generating means to irradiate greater amounts of X-rays at a time of radiography other than at the time of fluoroscopy;

X-ray/visible-light converting means for converting an X-ray image into visible light;

solid state imaging means including a two dimensional array having horizontal and vertical pixels, wherein electric charges accumulated in an imaging section thereof are vertically transferred to a horizontal transfer path directly, for receiving an X-ray image of visible light from said X-ray/visible-light converting means to form a radiographic image; and X-ray shielding means for controlling the width of an aperture window of said X-ray generating means to be variable in a direction perpendicular to the horizontal transfer path of said solid state imaging means in order to partially shield X-rays irradiated therefrom such that selected portions of the examinee are not irradiated with the X-rays.

7. The X-ray diagnostic apparatus according to claim 6, further comprising driving control means for controlling said solid state imaging means to read and sweep away the electric charges previously stored therein due to the dark current and corresponding to the shielded X-rays to a drain area via the horizontal transfer path, and to read and output as a radiographic image signal electric charges which correspond to unshielded X-rays from the horizontal transfer path.

8. The X-ray diagnostic apparatus according to claim 7, wherein said driving control means controls said solid state imaging means to stop reading electric charges in a frame upon completion of reading the electric charges which correspond to unshielded X-rays, and before reading electric charges in a next frame, to sweep away electric charges due to dark current and corresponding to the shielded X-rays in the frame together with electric charges due to dark current and corresponding to the shielded X-rays in the next frame to the drain area.

9. The X-ray diagnostic apparatus according to claim 6, further comprising driving control means f or controlling said solid state imaging means to read the electric charges in each horizontal line due to the dark current and corresponding to the shielded X-rays at high speed, to add all the electric chargers which correspond to the shielded X-rays on the horizontal transfer path, and then to sweep away the added electric charges which correspond to the shielded X-rays to a drain area via the horizontal transfer path, while sequentially reading and outputting electric charges in each horizontal line which corresponds to unshielded X-rays.

10. An X-ray diagnostic apparatus, comprising:

an X-ray tube configured to irradiate an examinee with X rays;

a controller configured to control said X-ray tube to irradiate X rays successively at a time of fluoroscopy and to control said X-ray tube to irradiate greater amounts of X rays at a time of radiography other than at the time of fluoroscopy;

an image intensifier configured to convert an X-ray image into visible light;

a fluoroscopic camera configured to receive the X-ray image of visible light at the time of the fluoroscopy in order to form a fluoroscopic image;

a radiographic camera configured to receive the X-ray image of visible light at the time of the radiography in order to form a radiographic image after sweeping away electric charges previously stored therein due to a dark current, wherein said radiographic camera includes a solid state image sensor including a two dimensional array having horizontal and vertical pixels, and is configured to directly and vertically transfer electric charges accumulated in an imaging section thereof to a horizontal transfer path, and has a greater number of pixels than the number of pixels of said fluoroscopic camera;

an optical path changing section configured to direct an optical path for the X-ray image of visible light from said image intensifier to the fluoroscopic camera or to the radiographic camera; and an X-ray shielding section configured to control the width of an aperture window of the X-ray tube to be variable in a direction perpendicular to the horizontal transfer path of the radiographic camera in order to partially shield the X rays irradiated therefrom such that selected portions of the examinee are shielded from being irradiated with the X-rays.

11. An X-ray diagnostic apparatus, comprising:

an X-ray tube configured to irradiate an examinee with X rays;

a controller configured to control said X-ray tube to irradiate X rays successively at a time of fluoroscopy and to control said X-ray tube to irradiate greater amounts of X rays at a time of radiography other than at the time of fluoroscopy;

an image intensifier configured to convert an X-ray image into visible light;

a camera including a two dimensional array having horizontal and vertical pixels, and an imaging section configured to transfer electric charges accumulated therein vertically and directly to a horizontal transfer path, and configured to receive an X-ray image of visible light from said image intensifier in order to form a radiographic image; and X-ray shielding section configured to control the width of an aperture window of the X-ray tube to be variable in a direction perpendicular to the horizontal transfer path of the imaging section in order to partially shield X-rays irradiated therefrom such that selected portions of the examinee are shielded from being irradiated with the X-rays.

12. An X-ray diagnostic method for diagnosing an examinee having a rectangular-shaped portion to be examined by an X-ray diagnostic apparatus including a fluoroscopic camera which receives the X-ray image of visible light at the time of fluoroscopy to form a fluoroscopic image and a radiographic camera which receives the X-ray image of visible light at the time of radiography to form a radiographic image wherein said radiographic camera includes a solid stat image sensor including a two dimensional array having horizontal and vertical pixels and is configured to directly and vertically transfer electric charges accumulated in an imaging section thereof to a horizontal transfer path, said rectangular-shaped portion having a length in a lateral direction shorter than a length of a side of an image plane of said radiographic camera, said method comprising the steps of:

locating said examinee such that the longitudinal direction of the rectangular-shaped portion coincides with a horizontal transfer path of said radiographic camera;

specifying fluoroscopy by an examiner;

directing an optical path for an X-ray image of visible light from an image intensifier to said fluoroscopic camera by an optical path changing section;

activating and controlling an X-ray tube to successively irradiate said examinee with X rays;

forming the fluoroscopic image by said fluoroscopic camera which receives the X-ray image of visible light through said image intensifier from said X-ray tube;

controlling the width of an aperture window of said X-ray tube to be variable in adirection perpendicular to the horizontal transfer path of said radiographic camera in order to partially shield the X rays irradiated therefrom such that only the rectangular-shaped portion is irradiated with the X-rays;

specifying radiography at a desirable timing by the examiner;

directing the optical path for the X-ray-image of visible light from said image intensifier to said radiographic camera by said optical path changing section;

controlling said X-ray tube to irradiate greater amounts of X rays than at the time of fluoroscopy; and forming the radiographic image by said radiographic camera which receives the X-ray image of visible light through said image intensifier from said X-ray tube.

13. The X-ray diagnostic method according to claim 12, wherein the rectangular-shaped portion is an esophagus.

14. An X-ray diagnostic method for diagnosing an examinee having a rectangular-shaped portion to be examined by an X-ray diagnostic apparatus including a radiographic camera which receives the X-ray image of visible light at the time of radiography to form a radiographic image wherein said radiographic camera includes a solid stat image sensor including a two dimensional array having horizontal and vertical pixels and is configured to directly and vertically transfer electric charges accumulated in an imaging section thereof to a horizontal transfer path, said rectangular-shaped portion having a length in a lateral direction shorter than a length of a side of an image plane of said radiographic camera, said method comprising the steps of:

locating said examinee such that the longitudinal direction of the rectangular-shaped portion coincides with a horizontal transfer path of said radiographic camera;

controlling the width of an aperture window of an X-ray tube to be variable in a direction perpendicular to the horizontal transfer path of said radiographic camera in order to partially shield the X rays irradiated therefrom such that only the rectangular-shaped portion is irradiated with the X-rays;

specifying radiography by an examiner;

controlling said X-ray tube to irradiate greater amounts of X rays than at the time of fluoroscopy; and forming the radiographic image by said radiographic camera which receives the X-ray image of visible light through an image intensifier from said X-ray tube.

15. The X-ray diagnostic method according to claim 14, wherein the rectangular-shaped portion is an esophagus.

* * * * *